US005817305A

United States Patent [19]

Hamilton et al.

[11] Patent Number: 5,817,305

[45] **Date of Patent: *Oct. 6, 1998**

[54] ANTI-INFLAMMATORY COMPOSITIONS AND METHODS

[75] Inventors: John Allan Hamilton, Kew; Prudence Hamilton Hart, Millswood, both of Australia

[73] Assignee: University Of Melbourne, Victoria, Australia

[ * ] Notice: The term of this patent shall not extend beyond the expiration date of Pat. No. 5,449,515.

[21] Appl. No.: 316,507

[22] Filed: Sep. 30, 1994

Related U.S. Application Data

[63] Continuation of Ser. No. 858,967, Jul. 14, 1992, Pat. No. 5,449,515.

[30] Foreign Application Priority Data

Nov. 21, 1989 [AU] Australia ................................ PJ 7503

[51] Int. Cl.$^{6}$ .................................................... A61K 45/05

[52] U.S. Cl. .......................................... 424/85.2; 530/351

[58] Field of Search ............................ 424/85.2; 530/351

[56] References Cited

U.S. PATENT DOCUMENTS 4,985,241 1/1991 Zimmerman et al. ................. 424/85.2

FOREIGN PATENT DOCUMENTS

AUA 4156389 3/1990 Australia .

WO8702990 5/1987 WIPO .

WO9005183 5/1990 WIPO .

OTHER PUBLICATIONS

Abbas, Am. J. Pathol., vol. 129(1), pp. 26–33, 1987.

Oppenheim et al. (editors), "Immunophysiology", Oxford Univ. Press, pp. 96–98, 1990.

Hamblin, "Lymphokines", IRL Press, pp. 26–28, 1989.

Stites et al., (editors), "Basic & Clin. Immunology", 7th Edition, Appleton & Lange, pp. 90–91, 1991.

Jones et al., "Bailliere's Clin. Haematology", vol. 2(1), Chap. 6, 1989.

Hart, et al. Proc. Natl. Acad. Sci. 86 3803–3807 (1989) "Potential Anti–inflammatory Effect of IL–4".

Schleimer, et al. *J. Immunol.* 143 (4) 1310–1317 (1989) "Regulation of Human Basophil Mediator . . . ".

Hart et al. *Lymphokine Research* 9 (2) 147–153 (1990) "Augmentation of Glucocorticoid Actions on Human . . . ".

*Primary Examiner*—Chhaya D. Sayala

*Attorney, Agent, or Firm*—Walter H. Dreger; Jan P. Brunelle; Flehr, Hohbach, Test Albritton & Herbert LLP

[57] ABSTRACT

Therapeutic compositions and methods for the treatment of inflammation are disclosed. The compositions comprise at least one anti-inflammatory drug in combination with the lymphokine interleukin-4 (IL-4), which components interact synergistically in the treatemement of inflammation. Methods for the treatment of inflammation comprise administering to a subject in need of such treatment an effective amount of at least one anti-inflammatory drug and IL-4.

12 Claims, 7 Drawing Sheets

ANTI-INFLAMMATORY COMPOSITIONS AND METHODS

This is a continuation of application Ser. No. 07/858,967 filed 14 Jul. 1992, now U.S. Pat. No. 5,449,515, which was a National Stage Filing of PCT No. PCT/AU90/00558, filed Nov. 21, 1990, which claimed priority to Australian patent application PJ7503, filed Nov. 21, 1989.

FIELD OF THE INVENTION

This invention relates to therapeutic compositions and methods for the treatment of inflammation.

BACKGROUND OF THE INVENTION

Inflammation is associated with many disease states, such as rheumatoid arthritis, psoriasis, asthma and allergies, and it is generally thought to be caused by inflammatory mediators such as interleukin-1 (IL-1), tumour necrosis factor-α (TNF-α), histamine and prostaglandin $E_2$ ($PGE_2$).

Therapeutics used for the treatment of inflammation fall into two principle classes, namely glucocorticoids and non-steroidal anti-inflammatory agents. Glucocorticoids (also known as corticosteroids) are among the most potent and widely used anti-inflammatory agents and include naturally occurring corticosteroids such as cortisone and hydrocortisone, and synthetic analogues such as betamethasone, dexamethasone, fluprednisolone, prednisone and paramethasone. Non-steroidal anti-inflammatory agents include aspirin, indomethacin, ibuprofen, phenylbutazone and diflusinal.

These prior therapeutic agents are often characterised by adverse side effects such as oedema, hypertension, osteoporosis, delayed wound healing, increased susceptibility to infection, menorrhea, liver disfunction, nausea and vomiting.

Interleukin-4 (IL-4), a product of activated T lymphocytes has a variety of stimulatory effects on B cells, T cells and mast cells and may be regarded as a proimmune, proinflammatory molecule. As described in International Patent Application No. WO 87/02990, IL-4 may stimulate mast cells to produce molecules such as histamines and prostaglandins. These agents have been implicated as inflammatory mediators.

To date, conventional compositions and methods for the treatment of inflammation have been associated with significant disadvantageous side effects as detailed above. Accordingly, a need exists for compositions and methods which avoid these disadvantages while providing effective treatment of inflammation.

SUMMARY OF THE INVENTION

The present invention solves the problems referred to above by providing therapeutic compositions and methods for treating inflammation. This invention is based on the surprising and unexpected finding that IL-4 and anti-inflammatory agents interact synergistically in the treatment of inflammation, that is, IL-4 potentiates the activity of steroidal and non-steroidal anti-inflammatory drugs. As a consequence, significantly less anti-inflammatory drug may be required in the treatment of inflammation, with a reduction in attendant side effects which typically characterise anti-inflammatory treatments.

According to one aspect of the present invention there is provided a composition for the treatment of inflammation which comprises:

(a) one or more anti-inflammatory drugs; and (b) IL-4;

optionally in the presence of one or more pharmaceutically acceptable carriers or excipients.

Figure 1:
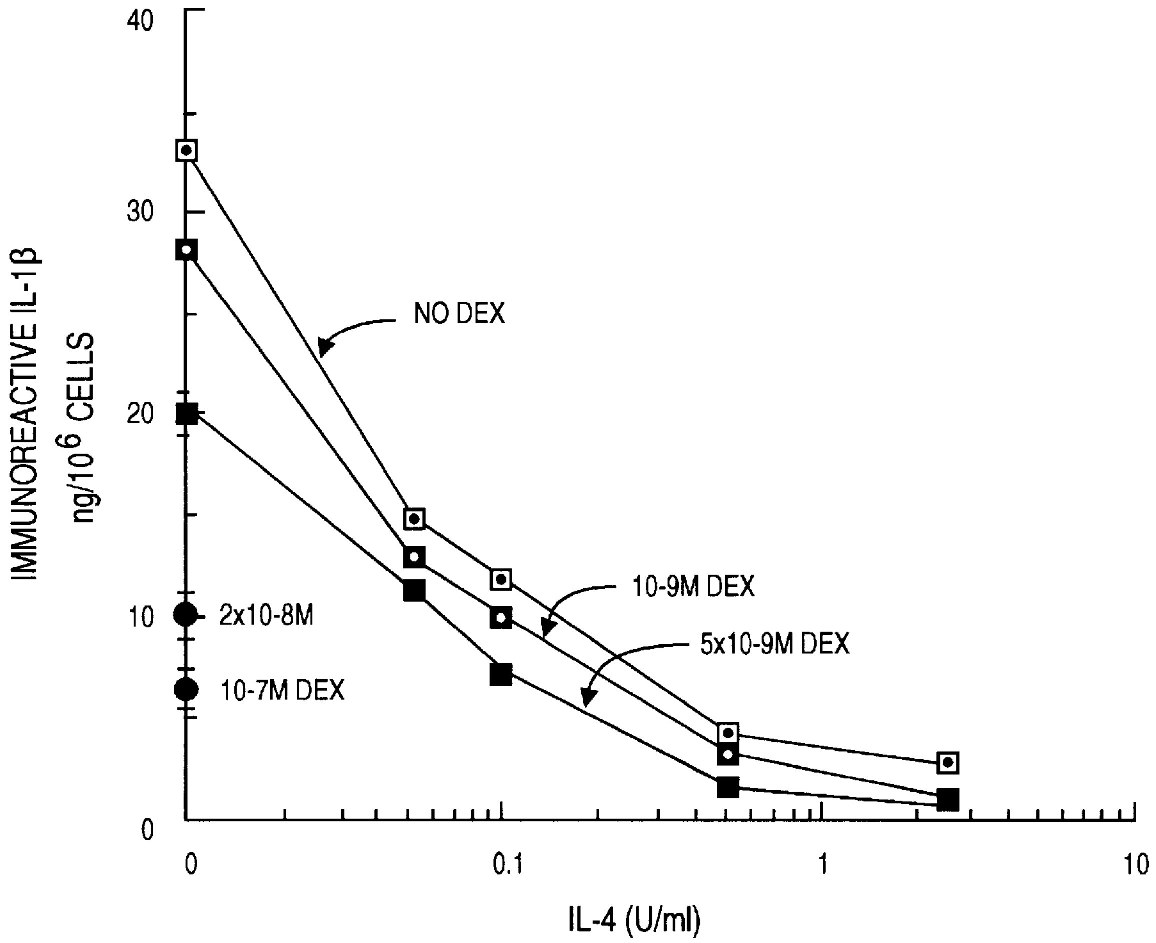
FIG. 1 shows the effects of IL-4 and dexamethasone (Dex) on the immunoreactive IL-1β levels of activated human monocytes.

FIG. **4*a*** shows the opposing effects of Dex on the plasminogen activator (PA) activities of activated monocytes.

FIG. **4*b*** shows the opposing effects of IL-4, with and without Dex, on the plasminogen activator (PA) activities of activated monocytes.

FIG. **5*a*** shows the effect of IL-4 and indomethacin on immunoreactive IL-1β levels for stimulated human monocytes.

FIG. **5*b*** shows the effect of IL-4 and indomethacin on immunoreactive TNFα levels for stimulated human monocytes.

DESCRIPTION OF THE PREFERRED EMBODIMENTS

As has been previously stated in this specification, anti-inflammatory drugs fall into the categories of glucocorticoids or steroidal anti-inflammatory agents, and non-steroidal anti-inflammatory agents. Any steroidal anti-inflammatory agent may be utilized in the present invention. For example, steroidal anti-inflammatory drugs may be selected from cortisone, betamethasone, dexamethasone, fluprednisolone, hydrocortisone, methylprednisolone, paramethasone, prednisolone, prednisone and triamcinolone. Any non-steroidal anti-inflammatory drug may also be utilized in the invention. For example, non-steroidal anti-inflammatory drugs may be selected from aspirin, inodomethacin, ibuprophen, phenylbutasone and diflusinal. Compositions may contain a combination of steroidal anti-inflammatory agents, non-steroidal anti-inflammatory agents, or both-steroidal and non-steroidal anti-inflammatory agents.

A preferred embodiment of the invention utilizes the set of glycosylated or unglycosylated human IL-4 proteins and muteins defined by the following formula: (SEQ ID NO:1)

Formula I (SEQ. ID no.1)

X(His)—X(Lys)—X(Cys)—X(Asp)—X(Ile)—X(Thr)—
X(Leu)—X(Gln)—X(Glu)—X(Ile)—X(Ile)—X(Lys)—
X(Thr)—X(Leu)—X(Asn)—X(Ser)—X(Leu)—X(Thr)—
X(Glu)—X(Gln)—X(Lys)—X(Thr)—X(Leu)—X(Cys)—
X(Thr)—X(Glu)—X(Leu)—X(Thr)—X(Val)—X(Thr)—
X(Asp)—X(Ile)—X(Phe)—X(Ala)—X(Ala)—X(Ser)—
X(Lys)—X(Asn)—X(Thr)—X(Thr)—X(Glu)—X(Lys)—
X(Glu)—X(Thr)—X(Phe)—X(Cys)—X(Arg)—X(Ala)—
X(Ala)—X(Thr)—X(Val)—X(Leu)—X(Arg)—X(Gln)—
X(Phe)—X(Tyr)—X(Ser)—X(His)—X(His)—X(Glu)—
X(Lys)—X(Asp)—X(Thr)—X(Arg)—X(Cys)—X(Leu)—
X(Gly)—X(Ala)—X(Thr)—X(Ala)—X(Gln)—X(Gln)—
X(Phe)—X(His)—X(Arg)—X(His)—X(Lys)—X(Gln)
X(Leu)—X(Ile)—X(Arg)—X(Phe)—X(Leu)—X(Lys)—
X(Arg)—X(Leu)—X(Asp)—X(Arg)—X(Asn)—X(Leu)—
X(Trp)—X(Gly)—X(Leu)—X(Ala)—X(Gly)—X(Leu)—

-continued

| Formula I (SEQ. ID no.1) |
|---|
| X(Asn)—X(Ser)—X(Cys)—X(Pro)—X(Val)—X(Lys)—<br>X(Glu)—X(Ala)—X(Asn)—X(Gln)—X(Ser)—X(Thr)—<br>X(Leu)—X(Glu)—X(Asn)—X(Phe)—X(Leu)—X(Glu)—<br>X(Arg)—X(Leu)—X(Lys)—X(Thr)—X(Ile)—X(Met)—<br>X(Arg)—X(Glu)—X(Lys)—X(Tyr)—X(Ser)—X(Lys)—<br>X(Cys)—X(Ser)—X(Ser) |

wherein the term X(Xaa) represents the group of synonymous amino acids to the amino acid Xaa. Synonymous amino acids within a group have sufficiently similar physicochemical properties for substitution between members of the group to preserve the biological function of the molecule: Grantham, *Science*, Vol. 185, ¶ 862–864 (1974). It is clear that insertions and deletions of amino acids may also be made in the above-defined sequence without altering biological function, particularly if the insertions or deletions only involve a few amino acids, e.g. under ten, and do not remove or displace amino acids which are critical to a functional conformation, e.g. cysteine residues, Anfinsen, "Principles That Govern The Folding of Protein Chains", *Science*, Vol. 181, ¶ 223–230 (1973). Proteins and muteins produced by such deletions and/or insertions come within the purview of the IL-4 utilized in the present invention. Whenever amino acid residues of the protein of Formula I (SEQ ID NO: 1) are referred to herein by number, such number or numbers are in reference to the N-terminus of the protein.

Preferably, the synonymous amino acid groups are those defined in Table I. More preferably, the synonymous amino acid groups are those listed before the second slash in each line in Table I; and most preferably the synonymous amino acid groups are those listed before the first slash in each line in Table II.

TABLE I

Preferred Groups of Synonymous Amino Acids.

| Amino Acid | Synonymous Group |
|---|---|
| Ser | Ser,//Thr, Gly, Asn |
| Arg | Arg,/His, Lys,/Glu, Gln |
| Leu | Leu, Ile, Met,/Phe,/Val, Tyr |
| Pro | Pro,/Ala/Thr, Gly |
| Thr | Thr,//Pro, Ser, Ala Gly, His, Gln |
| Ala | Ala/Pro,/Gly, Thr |
| Val | Val,/Met, Ile/Tyr, Phe, Leu Val |
| Gly | Gly,//Ala Thr, Pro, Ser |
| Ile | Ile, Met, Leu,/Phe, Val,/Ile, Tyr |
| Phe | Phe,/Met, Tyr, Ile, Leu,/Trp, Val |
| Tyr | Tyr,/Phe,/Trp, Met, Ile, Val, Leu, |
| Cys | Cys, Ser,//Thr |
| His | His/Gln, Arg,/Lys, Glu, Thr |
| Gln | Gln,/Glu, His,/Lys, Asn, Thr, Arg |
| Asn | Asn,/Asp,/Ser, Gln |
| Lys | Lys,/Arg,/Glu, Gln, His |
| Asp | Asp,/Asn,/Glu |
| Glu | Glu,/Gln,/Asp, Lys, Asn, His, Arg |
| Met | Met, Ile, Leu,/Phe, Val/ |

The IL-4 utilized in the present invention includes the polypeptides of Formula I with amino acid substitutions (between an amino acid of the native human IL-4 and a synonymous amino acid) at a single position or at multiple positions. The term "N-fold substituted" is used to describe a subset of polypeptides defined by Formula I wherein the native amino acids have been substituted by synonymous amino acids at least N positions. Thus, for example, the group of 1-fold substituted polypeptides of Formula I consists of 559 polypeptides for the preferred groups of synonymous amino acids, 189 for the more preferred groups of synonymous amino acids, and 56 for the most preferred groups of synonymous amino acids. These numbers were arrived at by summing the number of amino acids of each kind in the native chain times the size of the synonymous amino acid group for that amino acid. Preferably, the group of human IL-4 polypeptides consists of the 10-fold substituted polypeptides of Formula I; more preferably it consists of 3-fold substituted polypeptides of Formula I; and most preferably it consists of 1-fold substituted polypeptides of Formula I. International Patent Application No. WO 87/02990 is incorporated herein in its entirety by reference. Notwithstanding the above definition, IL-4 also refers to animal IL-4, a3 produced for example by mice, rats, horses, cats, dogs and sheep. The definition IL-4 includes all proteii c;, polypeptides and peptides which are natural or recombinant IL-4's or derivatives thereof having IL-4 activity which are characterised in having a potentiating activity on anti-inflammatory drugs in the treatment of inflammation. IL-4 derivatives are generally substitution, insertion or deletion variants of IL-4, wherein one or more amino acids are substituted, inserted or deleted into or from the "native" IL-4 amino acid sequence. The IL-4's used in the processes and compositions of this invention may be produced by purification from natural sources using conventional techniques or may be produced by recombinant DNA methodology. Generally IL-4 used in this invention is homogenous or substantially homogeneous, that is, is at least 95% and more preferably 99% pure as ascertained by analytical techniques such as polyacrylamide gel electrophoresis (PAGE) and high performance liquid chromatography (HPLC). For example, IL-4 may be produced according to the teachings of WO 87/02990 which, as mentioned previously, is incorporated herein by reference.

IL-4 and anti-inflammatory drugs, particularly steroidal antiinflammatory drugs, interact synergistically over a wide range of concentrations of both components, ranging from etuimolar amounts of IL-4 to steroid, to excess of steroid or excess of IL-4. Without limiting the invention in any way, the molar excess of anti-inflammatory agent over IL-4 in a therapeutic composition may for example be between $10^{0.5}$ to $10^4$.

In accordance with a further aspect of the present invention there is provided a method for the treatment of inflammation which comprises administering to a subject in need of such treatment a composition comprising a therapeutically effective amount of:

(i) one or more anti-inflammatory agents; and (ii) a synergistic amount of IL-4;

optionally in the presence of one or more pharmaceutically acceptable carriers or excipients.

The pharmaceutical composition may be administered in a convenient manner such as by the oral, intravenous, intramuscular, subcutaneous, intraperitoneal, intranasal, intradermal or suppository routes.

The composition also may be administered to a human or animal subject by continuous infusion over a predetermined time period, for example, for 30 minutes to 24 hours. Administration may be by way of an intravenous catheter connected to an appropriate pump, or by gravity feed.

The amounts of and dosage regimes of IL-4 and anti-inflammatory agents which are administered to a subject will depend on a number of factors such as the mode of administration, the nature of the condition being treated, the body weight of the subject being treated, and the judgement of the prescribing physician or veterinarian. Generally speaking, the anti-inflammatory agent and IL-4 may be administered in a combined amount between 0.1 μg to 2000 mg per kilogram of body weight per day. The quantity of the two components in a unit dosage such as a tablet or capsule may vary from about 0.1 μg to 100 mg, and the molar excess of anti-inflammatory agent(s) over IL-4 may be in the range $10^{0.5}$ to $10^4$.

IL-4 may be coated by, or administered with, a material to prevent its inactivation. For example, the active material may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water P40 emulsions as well as conventional liposomes.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, sterile water, ethanol, polyol (for example, glycerol, propylene glycol and liquid polyethylene glycol and the like), suitable mixtures thereof, and vegetable oils. The proper fluidity can be maintained, for example, by the use of a coating such as lecithin, by the maintenance of the required particle size in the case of a dispersion, and the use of surfactants. The preventions of the action of microorganisms can be brought about by various antibacterial and antifungal agents, for example, parabens, chlorobutanol, phenol, sorbic acid, thermerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active material in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When IL-4 is suitably protected as described above, the active compound may be orally administered, for example, with an inert diluent or with an edible carrier, or it may be enclosed in hard or soft shell gelatin capsule, or it may be compressed into tablets, or it may be incorporated directly with the food of the diet. For oral therapeutic administration, the active material may be incorporated with excipients and used in the form of ingestible tablets, buccal tablets, troches, capsules, elixirs, suspensions, syrups, wafers, and the like.

The tablets, troches, pills, capsules and the like may also contain the following: a binder such as gum tragacanth, acacia, coin starch or gelatin; excipients such as dicalcium phosphate; and disintegrating agents such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active material may be incorporated into sustained-release preparations and formulations.

As used herein, the terms "pharmaceutically acceptable carrier" and "excipient" include any and all solvents, dispersion media, coatings, antibacterial and antifungal agents, isotonic and absorption delaying agents, and the like described above. The use of such carriers and excipients is well known in the art, see for example, Remington's Pharmaceutical Science and U.S. Pharmacopeia (1984); Mack Publishing Company, Easton, Pa.

IL-4 and steroidal or non-steroidal anti-inflammatory drugs may be administered to a human patient or animal at the same time, or with a time interval between dosage application of each component. This time interval may range from a few seconds to several hours, and may extend from 12 to 24 hours. Therefore, according to a further aspect of this invention there is provided a method for the treatment of inflammation which comprises administering IL-4 and steroidal or non-steroidal drugs to a subject in need of such treatment.

By the present invention, the treatment of inflammation using steroid therapy may be supplemented with low amounts of IL-4 permitting the use of less steroid with concomitant reduction in side effects. This is a result of the synergistic interaction between IL-4 and steroid anti-inflammatory agents such that lesser amounts of steroid, such as 5 to 20 fold less, would be required for anti-inflammatory action.

As previously mentioned, IL-4 also potentiates the anti-inflammatory action of non-steroidal anti-inflammatory drugs. The biological mechanisms which underlies the potentiation of anti-inflammatory drug action with IL-4 are unclear. Without wishing to limit the invention in any way, insofar as non-steroidal anti-inflammatory drugs are concerned, it is believed that both IL-4 and the non-steroidal agents inhibit the production of cyclooxygenase products such as prostaglandins. In contrast to non-steroidal agents, IL-4 appears to inhibit the production of other inflammatory mediators such as TNF and IL-1. However, why the combined effects of these agents should be greater than that of each anti-inflammatory agent is uncertain. The mechanism behind the potentiation of steroidal action with IL-4 is also uncertain.

In a still further aspect of this invention, there is provided a method for the treatment of inflammation or other disorders usually treated with steroids, which method comprises administering to a subject in need of such treatment a therapeutically effective amount of interleukin-4 (IL-4).

This aspect of the invention is based on the finding that IL-4 may act as a steroid replacement. Particularly, the aforementioned compound acts to decrease the production of inflammatory mediators such as IL-1, IL-6, tumour necrosis factor-α (TNF-α), prostaglandin $E_2$ ($PGE_2$) and colony stimulating factors (GM-CSF and G-CSF).

The invention will now be describes with reference to the following non-limiting Figures and Example. The Examples show results on the production of inflammatory mediators, such as $PGE_2$, TFN-α and IL-1β by activated monocytes in culture, after stimulation with lypopolysaccharide (LPS) and IFN-γ in the presence of anti-inflammatory agents, IL-4, or combinations thereof, and clearly depict the synergy between IL-4 and anti-inflammatory agents in suppressing the production of anti-inflammatory mediators. This model system provides direct support for the in-vivo use of IL-4/anti-inflammatory drug combinations in the treatment of inflammation, and for the view that lower amounts of anti-inflammatory drugs would be required for effective therapy when they are administered in concert with IL-4.

Figure 2:
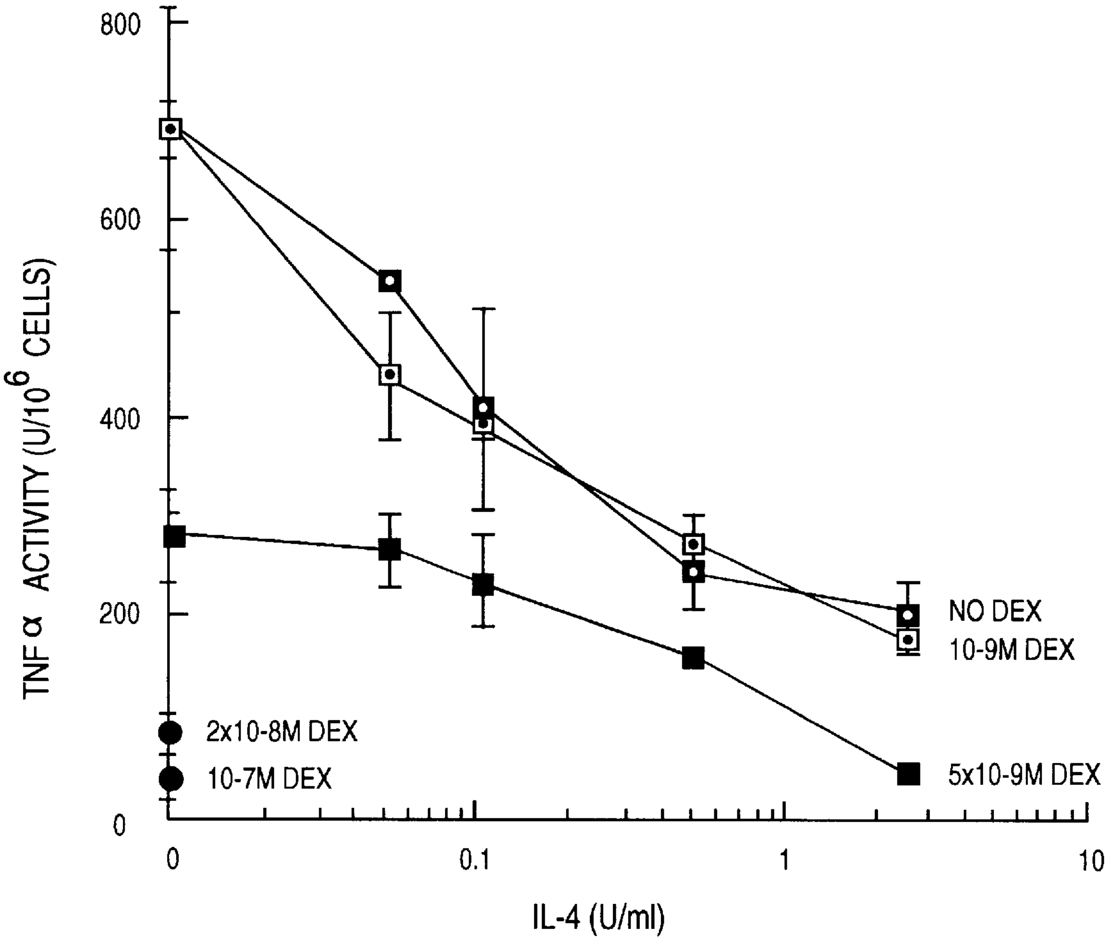
FIG. 2 shows the effects of IL-4 and Dex on the TNFα activities of activated human monocytes.
Figure 3:
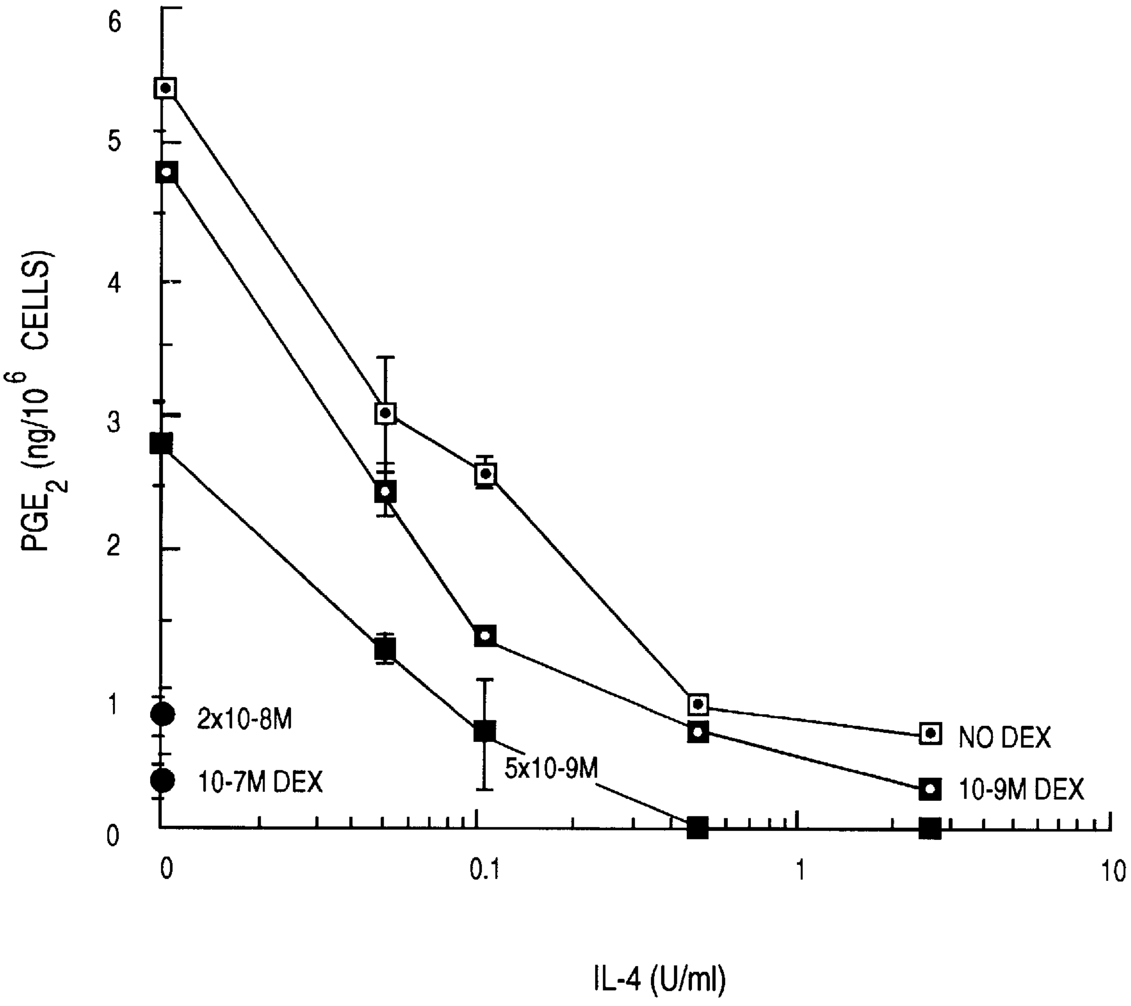
FIG. 3 shows the effects of IL-4 and Dex on the $PGE_2$ levels of activated human monocytes.
Figure 4A:
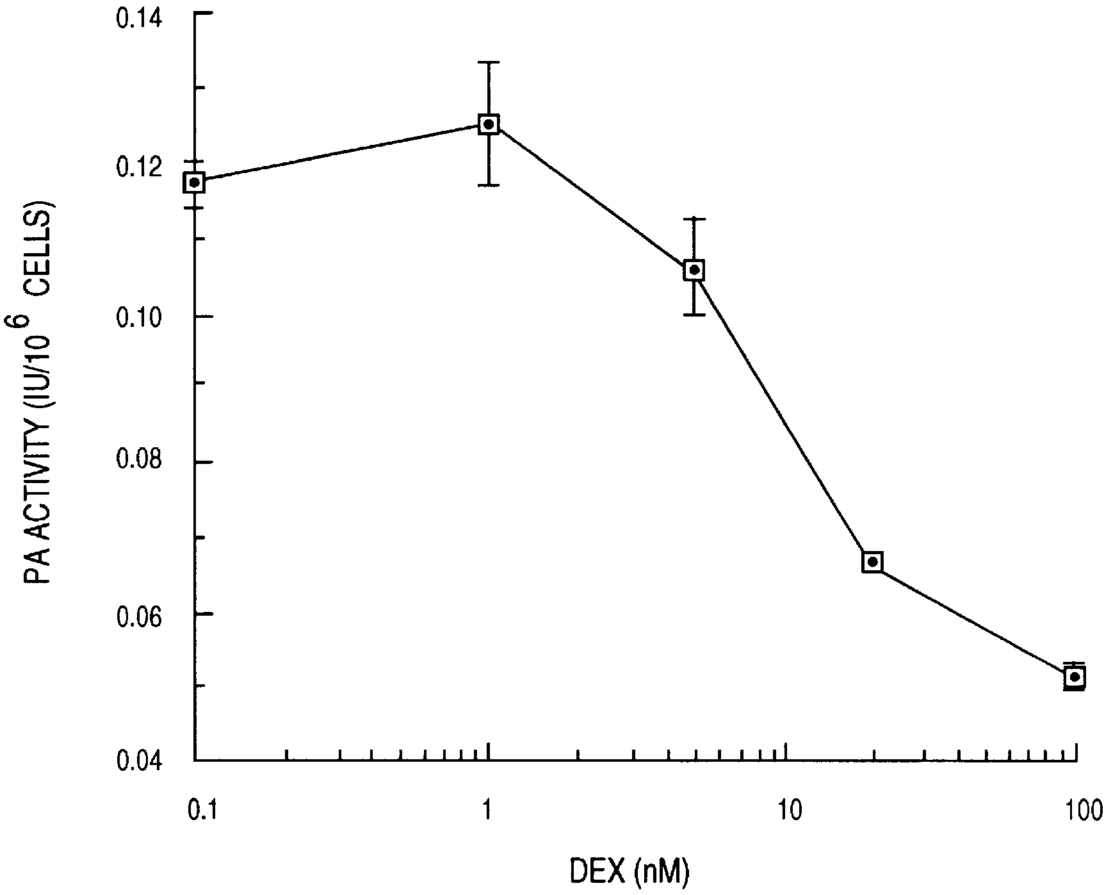

The Figures of this application show the following:

FIG. 1 shows the effects of IL-4 and Dex on the immunoreactive IL-1β levels of activated human monocytes from a representative donor. Monocytes are cultured for 18 h with LPS and IFN-γ, together with Dex and IL-4 as indicated. IL-1β levels were assayed by ELISA. The mean level±SEM for supernatants from triplicate cultures is shown; for many values the SEM was too small to be diagrammatically represented;

FIG. 2 shows the effects of IL-4 and Dex on the TNFα activities of activated human monocytes. TNFα activities were measured with actinomycin D-treated L929 target cells. Mean activities±SEM (n=3) were measured in the same supernatants for which IL-1β levels are shown in FIG. 1; for some measurements the SEM was too small to be diagrammatically represented;

FIG. 3 shows the effects of IL-4 and Dex on the $PGE_2$ levels of activated human monocytes. Levels of $PGE_2$ were determined by immunoassay. Mean levels±SEM (n=3) were measured in the same supernatants for which IL-1β levels and TNFα activities are shown in FIGS. 1 and 2 respectively; for some measurements the SEM was too small to be diagrammatically represented;

FIG. 4 shows the opposing effects of IL-4 and Dex on the PA activities of activated monocytes from a representative donor. PA activities were measured (A) in the supernatants of monocytes co-incubated with Dex alone (activity range 0.04–0.14 IU/$10^6$ cells), and (B) in the supernatants of monocytes co-incubated with both IL-4 and Dex (activity range 0–2.0 IU/$10^6$ cells). PA activities were assayed as described herein; greater than 95% of activity measured was plasminogen-dependent. Mean activities±SEM for triplicate cultures are shown; for some measurements the SEM was too small to be diagrammatically represented;

FIG. 5 shows the effect of IL-4 and Indomethacin on (A) immunoreactive IL-1β, and (B) immunoreactive TNFα levels for stimulated human monocytes. Monocytes from a different donor for whom results are shown in FIGS. 1 to 4 were isolated, cultured and stimulated as described; IL-1β was measured by ELISA and TNFA by radioimmunoassay. Mean levels±SEM for triplicate cultures are shown; however, for some measurements, the SEM was too small to be diagrammatically represented.

ABBREVIATIONS:

DEX—dexamethasone

IFN—interferon

IL—interleukin

LPS—lipopolysaccharide

PA—plasminogen activator

TNF—tumour necrosis factor

FCS—fetal calf serum

MAb—monoclonal antibody

EXAMPLE 1

Assays for IL-1, TNFα, $PGE_2$ and plasminogen activator were carried out according to the methods of Hart et al. (Proc. Natl. Acad. Sci. U.S.A. 86: 3803; Blood 74: 551; Immunology 66: 376; J. Immunol. 141: 1516) details of which are incorporated herein by reference in their entirety.

Monocyte Isolation and Culture:

Monocytes (≧95% purity) were isolated from peripheral venous blood by countercurrent centrifugal elutriation and cultured (0.8–1.0×$10^6$/ml) for 18 h in α-modified Eagle's medium containing 1% FCS. All monocytes were stimulated with LPS from *Escherichia coli* 0111:B4 (100 ng/ml, Difco Laboratories Inc., Detroit, Mich.) and human rIFN-γ (100 U/ml; Dr. E. Hochuli, Hoffmann-La Roche, Basel, Switzerland). Dex (Sigma Chemical Co., St. Louis, Mo.) was added at 0–$10^{-7}$M; IL-4 (Ms. A. Van Kimmenade, DNAX, Palo Alto, Calif.) was added at 0–2.5 U/ml.

Assays:

IL-1β levels were measured by an ELISA using mAb to IL-1β from Dr. A. C. Allison, Syntex, Palo Alto, Calif. A murine thymocyte comitogenesis assay was used to measure IL-1 bioactivity.

TNFα activities were measured with actinomycin D-treated L929 target cells and using a human rTNFα standard (Dr. G. R. Adolf, Ernst-Boehringer Institut, Vienna, Austria). Immunoreactive TNFα was measured by radioimmunoassay.

$PGE_2$ (≧0.03 ng/ml) was determined by immunoassay using competitive adsorption to dextran-coated charcoal ($PGE_2$ $^3$H/RIA Kit, Seragen, Boston, Mass.).

Plasminogen activator (PA) activity was assayed by measurement of $^{125}$I-fibrin degradation products and expressed according to the activity of a tissue-type PA (t-PA) standard (National Institute for Biological Standards and Control, London).

Experimental Results:

IL-1: The changes of IL-1β protein due to addition of IL-4 and Dex to monocytes stimulated with LPS and IFN-γ are shown in FIG. 1. IL-4 concentrations as low as 0.05 U/ml potentiated the action of Dex (1–5×$10^{-9}$M). When the mean levels for stimulated monocytes from four donors were compared, Dex ($10^{-7}$M) reduced the IL-1β levels from 11.8±5.6 ng/$10^6$ cells (means±SEM) to 2.5±1.1 ng/$10^6$ cells, while for Dex (5×$10^{-9}$M) with IL-4 (0.5 U/ml) the IL-1β levels were reduced to 1.0±0.4 ng/$10^6$ cells. Thus, 20 fold less DEX, in the presence of IL-4 showed significant inhibition of inflammatory mediators.

TNFα: When TNFα activities were quantified, 5×$10^{-9}$M Dex in the presence of 2.5 U IL-4/ml was as effective as $10^{-7}$M and 2×$10^{-8}$M Dex (FIG. 2). When the mean activities from triplicate cultures of monocytes isolated from four donors were compared, the TNFα activities induced by LPS with IFN-γ (478±188 U/$10^6$ cells, mean±SEM) were reduced by Dex ($10^{-7}$M) to 14±9 U/$10^6$ cells, whereas Dex (5×$10^{-9}$M) together with IL-4 (2.5 U/ml) reduced TNFα activities to 68±40 U/$10^6$ cells. Similar findings (data not shown) were obtained using an immunoassay for TNFα.

$PGE_2$: For monocyte $PGE_2$ production, similar results were obtained (FIG. 3). For four donors, LPS with IFN-γ induced 7.7±1.0 ng $PGE_2$/$10^6$ cells (mean±SEM). Dex ($10^-$ 7M) lowered $PGE_2$ levels to 0.3±0.1 ng/$10^6$ cells, while Dex ($5\times10^{-9}$M) with IL-4 (0.5 U/ml) reduced $PGE_2$ levels to 0.4±0.2 ng/$10^6$ cells.

Figure 4B:
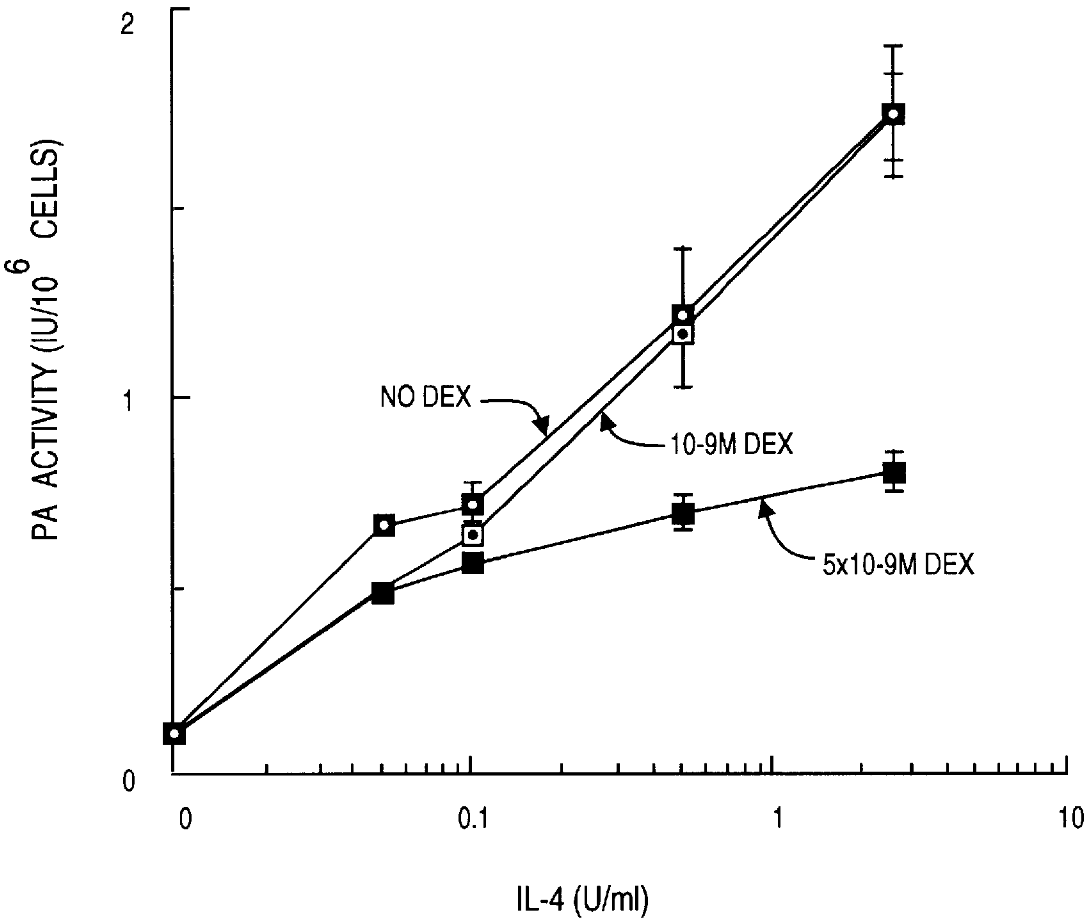

Tissue Plasminogen Activator: Dex and IL-4 do not always potentiate the action of each other on monocyte product synthesis. PA activity was measured in the same supernatants which were used to obtain the data presented in FIGS. 1 to 3. Whereas increasing concentrations of Dex suppressed the action of LPS with IFN-γ for enhanced PA activity (FIG. 4A), increasing concentrations of IL-4 potentiated it and opposed the suppressive effects of Dex (FIG. 4B). This observation was confirmed in four donors. We also confirmed that detectable PA activity in the monocyte supernatants was t-PA and not urokinase-type PA (u-PA) by SDS-PAGE zymography and by antibody blocking and depletion of t-PA activity.

Figure 5A:
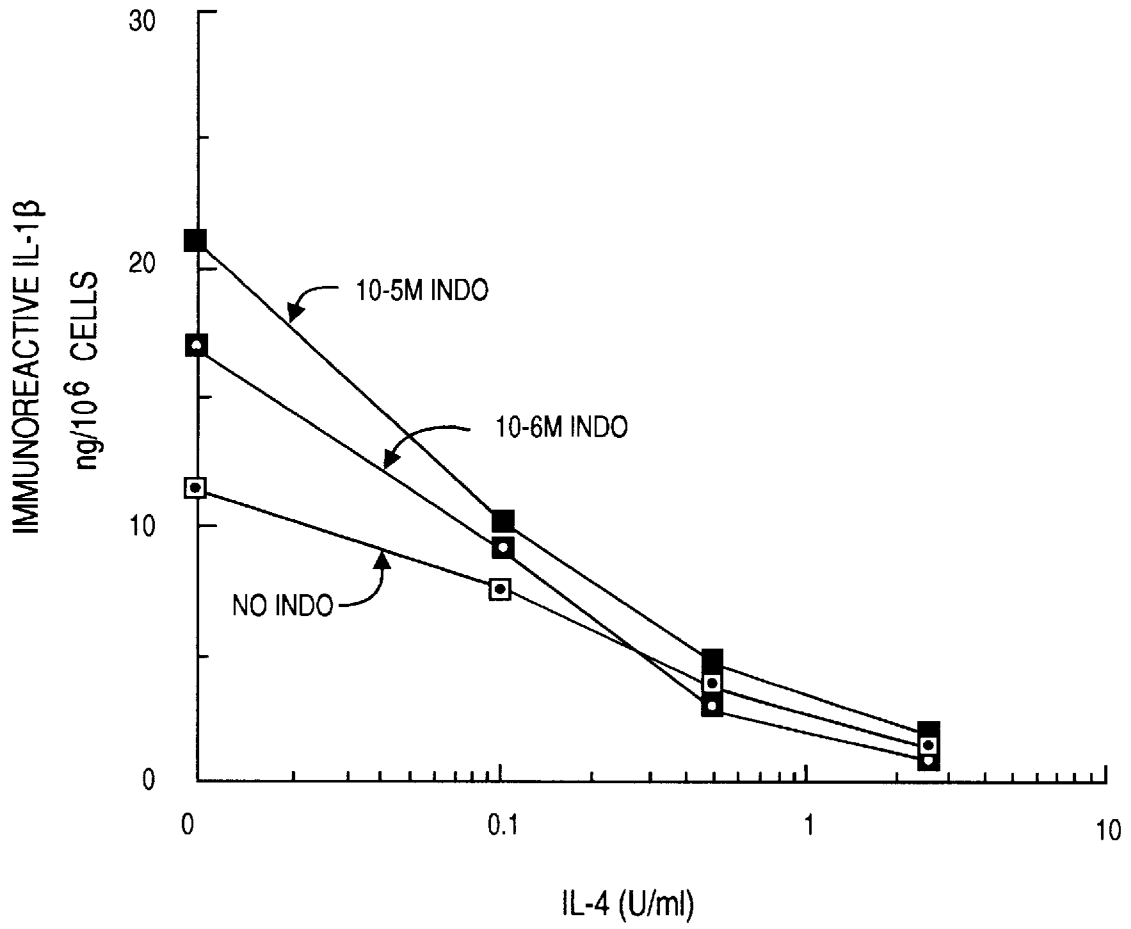
Figure 5B:
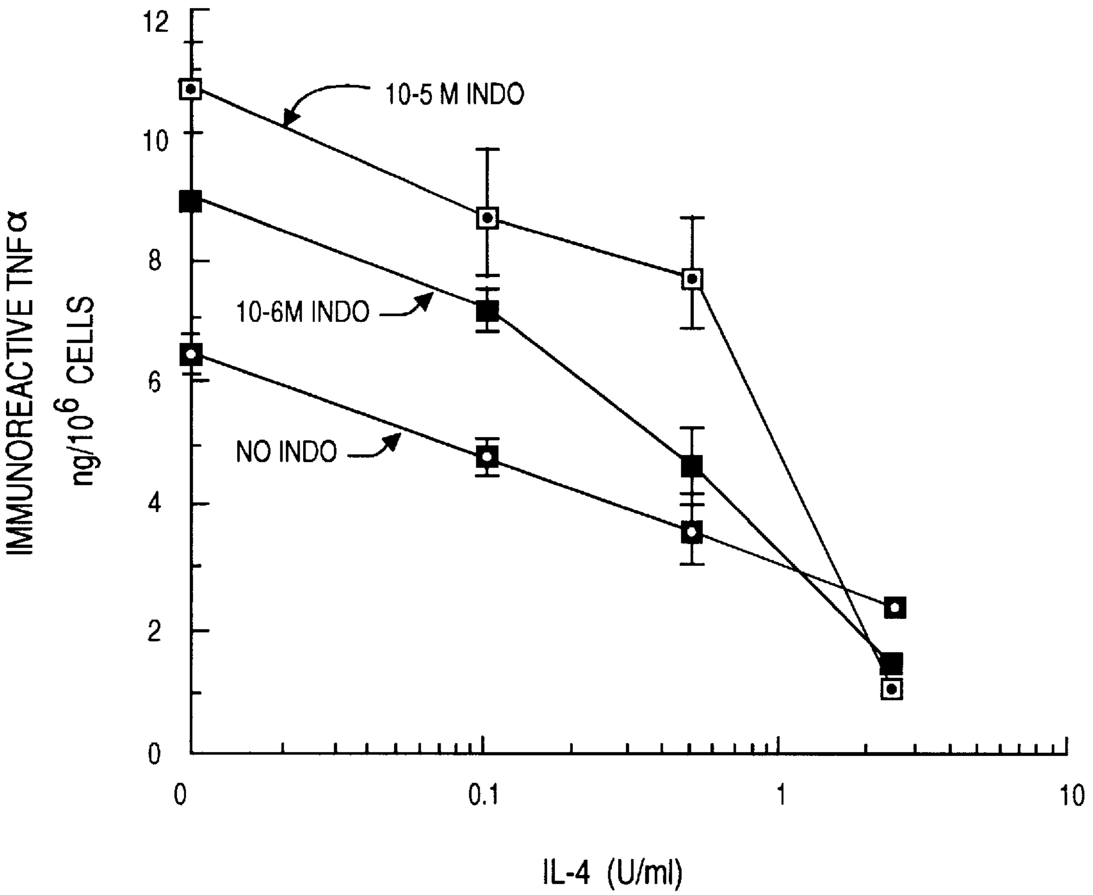

IL-4 and Non-Steroidal Anti-Inflammatory Agents:

We have found previously that endogenous cyclooxygenase products inhibit partially the production of IL-1 and TNFα by stimulated human monocytes (Hart, et al., Immunology 66: 736). Thus, non-steroidal anti-inflammatory drugs which suppress cyclooxygenase product formation, paradoxically enhance the levels of these pro-inflammatory mediators. FIGS. 5A and 5B confirm these observations for monocytes stimulated by LPS and IFN-γ, $\geqq 10^{-6}$M indomethacin completely suppressed $PGE_2$ production (data not shown). On addition of IL-4 at 0.1 and 2.5 U/ml to non-indomethacin-treated cells, the $PGE_2$ levels induced by LPS with IFN-γ fell from 14.7 ng/$10^6$ cells to 9.5 and 1.4 ng/$10^6$ cells, respectively, when the values were averaged for triplicate cultures of monocytes from the two donors studied. Thus, in response to 2.5 U IL-4/ml when minimal $PGE_2$ production occurred; the increases in IL-1β and TNFα levels measured in response to indomethacin were removed (FIGS. 5A and 5B).

These results show that when low concentrations of IL-4 and Dex are added together to cultures of activated monocytes, the resultant inhibition of the synthesis of IL-1, TNFα and $PGE_2$ is significantly greater than if either agent were added alone. To what extent the biochemical mechanisms involved in the inhibitory actions of IL-4 on monocyte product synthesis are similar to those involved in glucocorticoid-mediated regulation is unclear. Given the wide-ranging but often adverse effects of glucocorticoid treatment, it is encouraging that IL-4 has at least one different action to Dex on the monocyte, viz. the opposite effect on the production of the fibrinolytic enzyme, t-PA (FIG. 4). This t-PA-inducing property of IL-4 may further support its use with glucocorticoids because there is evidence that fibrin formed as a result of lymphokine activation of monocyte/macrophage procoagulant activity, may play a role in immune reactions associated with disease such as rheumatoid arthritis, glomerular nephritis and granulomatous disease.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps of features.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 129 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Modified-site
( B ) LOCATION: 1..2
( D ) OTHER INFORMATION: /note= "The amino acid at positions 1, 58, 59, 74 and 76 can represent any one of the group consisting of HIS, GLN, ARG, LYS, GLU, and THR."

( i x ) FEATURE:
( A ) NAME/KEY: Modified-site
( B ) LOCATION: 2..3
( D ) OTHER INFORMATION: /note= "The amino acid at positions 2, 12, 21, 37, 42, 61, 77, 84, 102, 117, 125 and 126 can represent any one of the group consisting of LYS, ARG, GLU, GLN, and HIS."

( i x ) FEATURE:
( A ) NAME/KEY: Modified-site
( B ) LOCATION: 3..4
( D ) OTHER INFORMATION: /note= "The amino acid at positions 3, 24, 46, 65, 99 and 127 can represent any one of the group consisting of CYS, SER and THR."

( i x ) FEATURE:
( A ) NAME/KEY: Modified-site
( B ) LOCATION: 4..5
( D ) OTHER INFORMATION: /note= "The amino acid at positions 4, 31, 62 and 87 can represent any one of the group consisting of ASP, ASN and GLU."

( i x ) FEATURE:
( A ) NAME/KEY: Modified-site
( B ) LOCATION: 5..6
( D ) OTHER INFORMATION: /note= "The amino acid at positions 5, 10, 11, 32, 80 and 119 can represent any one of the group consisiting of ILE, MET, LEU, PHE, VAL and TYR."

( i x ) FEATURE:
( A ) NAME/KEY: Modified-site
( B ) LOCATION: 6..7
( D ) OTHER INFORMATION: /note= "The amino acid at positions 6, 13, 18, 22, 25, 28, 30, 39, 40, 44, 50, 63, 69 108 and 118 can represent any one of the group consisting of THR, PRO, SER, ALA, GLY, HIS and GLN."

( i x ) FEATURE:
( A ) NAME/KEY: Modified-site
( B ) LOCATION: 7..8
( D ) OTHER INFORMATION: /note= "The amino acid at positions 7, 14, 17, 23, 27, 52, 66, 79, 83, 86, 90, 93, 96, 109, 113, and 116 can represent any one of the group consisting of LEU, ILE, MET, PHE, VAL and TYR."

( i x ) FEATURE:
( A ) NAME/KEY: Modified-site
( B ) LOCATION: 8..9
( D ) OTHER INFORMATION: /note= "The amino acid at positions 8, 20, 54, 71, 72, 78, and 106 can represent any one of the group consisting of GLN, GLU, HIS, LYS, ASN, THR, AND ARG."

( i x ) FEATURE:
( A ) NAME/KEY: Modified-site
( B ) LOCATION: 9..10
( D ) OTHER INFORMATION: /note= "The amino acid at positions 9, 19, 26, 41, 44, 60, 103, 110, 114, and 122 can represent any one of the group consisting of GLU, GLN, ASP, LYS, ASN, HIS and ARG."

( i x ) FEATURE:
( A ) NAME/KEY: Modified-site
( B ) LOCATION: 15..16
( D ) OTHER INFORMATION: /note= "The amino acid at positions 15, 38, 89, 97, 105, and 111 can represent any one of the group consisting of ASN, ASP, SER, and GLN."

( i x ) FEATURE:
( A ) NAME/KEY: Modified-site
( B ) LOCATION: 16..17
( D ) OTHER INFORMATION: /note= "The amino acid at positions 16, 36, 57, 98, 107, 125, 128, and 129 can represent any one of the group consisting of SER, THR, GLY and ASN."

( i x ) FEATURE:
( A ) NAME/KEY: Modified-site
( B ) LOCATION: 29..30
( D ) OTHER INFORMATION: /note= "The amino acid at positions 29, 51, and 101 can represent any one of the group consisting of VAL, MET, ILE, TYR, PHE, and LEU."

( i x ) FEATURE:
( A ) NAME/KEY: Modified-site
( B ) LOCATION: 33..34
( D ) OTHER INFORMATION: /note= "The amino acid at positions 33, 45, 55, 73, 82, and 112 can represent any one of the group consisting of PHE, MET, TYR, ILE, LEU, TRP AND VAL."

( i x ) FEATURE:
( A ) NAME/KEY: Modified-site
( B ) LOCATION: 47..48

-continued ( D ) OTHER INFORMATION: /note= "The amino acid at positions 47, 53, 75, 81, 85, 88, 115, and 121 can represent any one of the group consisting of ARG, HIS, LYS, GLU, and GLN."

( i x ) FEATURE:
( A ) NAME/KEY: Modified-site
( B ) LOCATION: 48..49
( D ) OTHER INFORMATION: /note= "The amino acid at positions 48, 49, 68, 70, 94, and 104 can represent any one of the group consisting of ALA, PRO, GLY, and THR."

( i x ) FEATURE:
( A ) NAME/KEY: Modified-site
( B ) LOCATION: 67..68
( D ) OTHER INFORMATION: /note= "The amino acid at positions 67, 92, and 95 can represent any one of the group consisting of GLY, ALA, THR, PRO, and SER."

( i x ) FEATURE:
( A ) NAME/KEY: Modified-site
( B ) LOCATION: 100..101
( D ) OTHER INFORMATION: /note= "The amino acid at position 100 can represent any one of the group consisting of PRO, ALA, THR, and GLY."

( i x ) FEATURE:
( A ) NAME/KEY: Modified-site
( B ) LOCATION: 120..121
( D ) OTHER INFORMATION: /note= "The amino acid at position 120 can represent any one of the group consisting of MET, ILE, LEU, PHE, and VAL."

( i x ) FEATURE:
( A ) NAME/KEY: Modified-site
( B ) LOCATION: 124..125
( D ) OTHER INFORMATION: /note= "The amino acid at position 124 can represent any one of the group consisting of TYR, PHE, TRP, MET, ILE, VAL, and LEU."

( x i ) SEQUENCE DESCRIPTION: SEQ ID NO:1:

| | | | | | | | | | | | | | | | |
|---|---|---|---|---|---|---|---|---|---|---|---|---|---|---|---|
| Xaa | Xaa | Xaa | Xaa | Xaa | Xaa | Xaa | Xaa | Xaa | Xaa | Xaa | Xaa | Xaa | Xaa | Xaa | Xaa |
| 1 | | | | 5 | | | | | 10 | | | | | 15 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 20 | | | | | 25 | | | | | 30 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 35 | | | | | 40 | | | | | 45 | | | |
| Xaa | Xaa | Xaa | Xaa | Xaa | Xaa | Xaa | Xaa | Xaa | Xaa | Xaa | Xaa | Xaa | Xaa | Xaa | Xaa |
| | 50 | | | | | 55 | | | | | 60 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 65 | | | | | 70 | | | | | 75 | | | | | 80 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 85 | | | | | 90 | | | | | 95 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 100 | | | | | 105 | | | | | 110 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 115 | | | | | 120 | | | | | 125 | | | |
| Xaa | | | | | | | | | | | | | | | |

We claim:

1. A composition for the treatment of inflammation which comprises a therapeutically effective amount of at least one anti-inflammatory drug and a synergistic amount of at least one conservative substitution variant of IL-4 that has a potentiating effect on said anti-inflammatory drug, said at least one conservative substitution variant having an amino acid sequence defined by Formula I wherein:

each X(Cys) represents an amino acid selected from the group consisting of Cys, Ser, and Thr;

X(Trp) represents Trp;

each X(Ser) represents an amino acid selected from the group consisting of Ser, Thr, Gly, and Asn;

each X(Arg) represents an amino acid selected from the group consisting of Arg, His, Gln, Lys, and Glu;

each X(Leu) represents an amino acid selected from the group consisting of Leu, Ile, Phe, Tyr, Met, and Val;

X(Pro) represents an amino acid selected from the group consisting of Pro, Gly, Ala, and Thr;

each X(Thr) represents an amino acid selected from the group consisting of Thr, Pro, Ser, Ala, Gly, His, and Gln;

each X(Ala) represents an amino acid selected from the group consisting of Ala, Gly, Thr, and Pro;

each X(Val) represents an amino acid selected from the group consisting of Val, Met, Tyr, Phe, Ile, and Leu;

each X(Gly) represents an amino acid selected from the group consisting of Gly, Ala, Thr, Pro, and Ser;

each X(Ile) represents an amino acid selected from the group consisting of Ile, Met, Tyr, Phe, Val, and Leu;

each X(Phe) represents an amino acid selected from the group consisting of Phe, Trp, met, Tyr, Ile, Val, and Leu;

each X(Tyr) represents an amino acid selected from the group consisting of Tyr, Trp, Met, Phe, Ile, Val, and Leu;

each X(His) represents an amino acid selected from the group consisting of His, Glu, Lys, Gin, Thr, and Arg;

each X(Gln) represents an amino acid selected from the group consisting of Gln, Glu, Lys, Asn, His, Thr, and Arg;

each X(Asn) represents an amino acid selected from the group consisting of Asn, Asp, Gln, and Ser;

each X(Lys) represents an amino acid selected from the group consisting of Lys, Glu, Gln, His, and Arg;

each X(Asp) represents an amino acid selected from the group consisting of Asp, Glu, and Asn;

each X(Glu) represents an amino acid selected from the group consisting of Glu, Asp, Lys, Asn, Gln, His, and Arg; and X(Met) represents an amino acid selected from the group consisting of Met, Phe, Ile, Val, and Leu.

2. A method for the treatment of inflammation which comprises administering to a subject in need of such treatment a therapeutically effective amount of a composition which comprises at least one anti-inflammatory drug and a synergistic amount of at least one conservative substitution variant of IL-4 that has a potentiating effect on said anti-inflammatory drug, said at least one conservative substitution variant having an amino acid sequence defined by Formula I wherein:

each X(Cys) represents an amino acid selected from the group consisting of Cys, Ser, and Thr;

X(Trp) represents Trp;

each X(Ser) represents an amino acid selected from the group consisting of Ser, Thr, Gly, and Asn;

each X(Arg) represents an amino acid selected from the group consisting of Arg, His, Gln, Lys, and Glu;

each X(Leu) represents an amino acid selected from the group consisting of Leu, Ile, Phe, Tyr, Met, and Val;

X(Pro) represents an amino acid selected from the group consisting of Pro, Gly, Ala, and Thr;

each X(Thr) represents an amino acid selected from the group consisting of Thr, Pro, Ser, Ala, Gly, His, and Gln;

each X(Ala) represents an amino acid selected from the group consisting of Ala, Gly, Thr, and Pro;

each X(Val) represents an amino acid selected from the group consisting of Val, Met, Tyr, Phe, Ile, and Leu;

each X(Gly) represents an amino acid selected from the group consisting of Gly, Ala, Thr, Pro, and Ser;

each X(Ile) represents an amino acid selected from the group consisting of Ile, Met, Tyr, Phe, Val, and Leu;

each X(Phe) represents an amino acid selected from the group consisting of Phe, Trp, met, Tyr, Ile, Val, and Leu;

each X(Tyr) represents an amino acid selected from the group consisting of Tyr, Trp, Met, Phe, Ile, Val, and Leu;

each X(His) represents an amino acid selected from the group consisting of His, Glu, Lys, Gln, Thr, and Arg;

each X(Gln) represents an amino acid selected from the group consisting of Gln, Glu, Lys, Asn, His, Thr, and Arg;

each X(Asn) represents an amino acid selected from the group consisting of Asn, Asp, Gln, and Ser;

each X(Lys) represents an amino acid selected from the group consisting of Lys, Glu, Gln, His, and Arg;

each X(Asp) represents an amino acid selected from the group consisting of Asp, Glu, and Asn;

each X(Glu) represents an amino acid selected from the group consisting of Glu, Asp, Lys, Asn, Gln, His, and Arg; and X(Met) represents an amino acid selected from the group consisting of Met, Phe, Ile, Val, and Leu.

3. A composition according to claim 1 wherein said anti-inflammatory drug is a steroidal anti-inflammatory.

4. A composition according to claim 3 wherein said steroidal anti-inflammatory is selected from cortisone, betamethasone, dexamethasone, fluprednisolone, hydrocortisone, methylprednisolone, paramethasone, prednisolone, prednisone and triamcinolone.

5. A composition according to claim 1 wherein said anti-inflammatory drug is a non-steroidal anti-inflammatory.

6. A composition according to claim 5, wherein said non-steroidal anti-inflammatory is selected from aspirin, inodomethacin, ibuprophen, phenylbutasone and diflusinal.

7. A composition according to claim 3 further comprising a non-steroidal anti-inflammatory.

8. A composition according to claim 1 further comprising one or more pharmaceutically acceptable carriers.

9. A method according to claim 2 wherein the inflammation is associated with an ailment selected from the group consisting of rheumatoid arthritis, psoriasis, asthma, and allergy.

10. A composition according to claim 1 wherein said conservative substitution variant of IL-4 is a 1-fold substitution variant.

11. A composition according to claim 1 wherein:

each X(Cys) represents an amino acid selected from the group consisting of Cys and Ser;

X(Ser) is Ser;

each X(Arg) represents an amino acid selected from the group consisting of Arg, His, and Lys;

each X(Leu) represents an amino acid selected from the group consisting of Leu, Ile, Phe, and Met;

X(Pro) represents an amino acid selected from the group consisting of Pro and Ala;

X(Thr) is Thr;

each X(Ala) represents an amino acid selected from the group consisting of Ala and Pro;

each X(Val) represents an amino acid selected from the group consisting of Val, Met, and Ile;

X(Gly) is Gly;

each X(Ile) represents an amino acid selected from the group consisting of Ile, Met, Leu, Phe, and Val;

each X(Phe) represents an amino acid selected from the group consisting of Phe, Met, Tyr, Ile, and Leu;

each X(Tyr) represents an amino acid selected from the group consisting of Tyr and Phe;

each X(His) represents an amino acid selected from the group consisting of His, Gln, and Arg;

each X(Gln) represents an amino acid selected from the group consisting of Gln, Glu, and His;

each X(Asn) represents an amino acid selected from the group consisting of Asn and Asp;

each X(Lys) represents an amino acid selected from the group consisting of Lys and Arg;

each X(Asp) represents an amino acid selected from the group consisting of Asp and Asn; and each X(Glu) represents an amino acid selected from the group consisting of Glu and Gln.

12. A composition according to claim 11 wherein:

X(Arg) is Arg;

each X(Leu) represents an amino acid selected from the group consisting of Leu, Ile, and Met;

X(Pro) is Pro;

X(Ala) is Ala;

X(Val) is Val;

each X(Ile) represents an amino acid selected from the group consisting of Ile, Met, and Leu;

X(Phe) is Phe;

X(Tyr) is Tyr;

X(His) is His;

X(Gln) is Gln;

X(Asn) is Asn;

X(Lys) is Lys;

X(Asp) is Asp;

X(Glu) is Glu; and

X(Met) represents an amino acid selected from the group consisting of Met, Ile, and Leu.

* * * * *